(12) United States Patent
Delaire et al.

(10) Patent No.: US 9,067,908 B2
(45) Date of Patent: Jun. 30, 2015

(54) POLYPHENOLIC BIOPRECURSORS

(75) Inventors: Sabine Delaire, Rueil Malmaison (FR); Adrien Adao, Opio (FR); Jean-Roger Desmurs, Cannes (FR); Mirjana Gelo-Pujic, Serezin du Rhone (FR); Laurent Saint-Jalmes, Vourles (FR); Tarek Kassem, Montpellier (FR)

(73) Assignees: RHODIA CHIMIE, Aubervilliers (FR); CHANEL PARFUMS BEAUTE, Neuilly sur Seine (FR)

( * ) Notice: Subject to any disclaimer, the term of this patent is extended or adjusted under 35 U.S.C. 154(b) by 2138 days.

(21) Appl. No.: 11/922,331

(22) PCT Filed: Jun. 16, 2006

(86) PCT No.: PCT/FR2006/001375
§ 371 (c)(1),
(2), (4) Date: Feb. 11, 2009

(87) PCT Pub. No.: WO2006/134282
PCT Pub. Date: Dec. 21, 2006

(65) Prior Publication Data
US 2009/0215881 A1  Aug. 27, 2009

(30) Foreign Application Priority Data
Jun. 17, 2005 (FR) .................... 05 06169

(51) Int. Cl.
| C07D 311/72 | (2006.01) |
| A61K 8/37 | (2006.01) |
| A61Q 19/00 | (2006.01) |
| C07C 39/21 | (2006.01) |
| C07C 69/40 | (2006.01) |
| C07C 69/587 | (2006.01) |
| C07C 69/734 | (2006.01) |
| C07C 69/88 | (2006.01) |
| C07C 69/92 | (2006.01) |
| C07D 339/04 | (2006.01) |

(52) U.S. Cl.
CPC .............. *C07D 311/72* (2013.01); *A61K 8/375* (2013.01); *A61K 2800/522* (2013.01); *A61Q 19/00* (2013.01); *C07C 39/21* (2013.01); *C07C 69/40* (2013.01); *C07C 69/587* (2013.01); *C07C 69/734* (2013.01); *C07C 69/88* (2013.01); *C07C 69/92* (2013.01); *C07D 339/04* (2013.01)

(58) Field of Classification Search
CPC .............................. A61K 8/375; C07D 311/72
USPC ......................................................... 514/183
See application file for complete search history.

(56) References Cited

U.S. PATENT DOCUMENTS

| 5,932,232 A | 8/1999 | De Salvert et al. |
| 7,345,090 B2 | 3/2008 | Pfluecker et al. |
| 2002/0106338 A1* | 8/2002 | Pfluecker et al. ............... 424/59 |

FOREIGN PATENT DOCUMENTS

| EP | 0487404 A1 | 5/1992 |
| EP | 0710478 A1 | 5/1996 |
| EP | 1205475 A1 | 5/2002 |

OTHER PUBLICATIONS

Saito et al., "Systematic synthesis of galloyl-substituted procyanidin B1 and B2, and their ability of DPPH radical scavenging activity and inhibitory activity of DNA polymerases", Bioorganic & Medical Chemistry, 2005, pp. 2759-2771, vol. 13, No. 8, www.sciencedirect.com.

Kamara et al., Phenolic Metabolites from Honeybush Tea (*Cyclopia subternata*), J. Argic. Food Chem., 2004, pp. 5391-5395, vol. 52, No. 17, American Chemical Society.

* cited by examiner

*Primary Examiner* — Yong Chong
(74) *Attorney, Agent, or Firm* — Dentons US LLP

(57) ABSTRACT

Cosmetic and therapeutic, in particular dermatological bioprecursors have the formula $[A]_n$-PP-$[B]_m$ wherein PP is a polyphenol radical in which each hydroxyl function is protected by a group A or a group B, A is a saturated or unsaturated, substituted or unsubstituted alkyl radical having 1 to 20 carbon atoms which is bonded to the polyphenol, $\underline{n}$ is an integer not less than 1, and B is a precursor of a biologically active molecule, which is also bonded to the polyphenol, and $\underline{m}$ is an integer also not less than 1.

23 Claims, No Drawings

POLYPHENOLIC BIOPRECURSORS

CROSS-REFERENCE TO PRIORITY/PCT APPLICATIONS

This application is the national stage of PCT/FR 2006/001375, filed Jun. 16, 2006 and designating the United States (published in the French language on Dec. 21, 2006, as WO 2006/134282 A1; the title and abstract were also published in English), which claims foreign priority of FR 05/06169, filed Jun. 17, 2005, each hereby expressly incorporated by reference in its entirety and each assigned to the assignee hereof.

The invention relates to bioprecursors of biologically active molecules for cosmetic or therapeutic use. It relates in particular to uses of the said bioprecursors of molecules for cosmetic or dermatological use. It also relates to compositions containing such precursors and to associated methods of treatment.

The range of cosmetic and/or dermatological compositions is very extensive. Amongst the active constituents most often used in these compositions, mention may be made of vitamins, such as vitamins A, B, C, D, E and F used for their properties against excess weight, ageing of the skin, dryness thereof, pigmentation thereof, acne and certain diseases of the skin such as psoriasis or also for promoting healing or restructuring of the skin.

Antioxidants are widely used in personal care products. The most frequently used antioxidants are tocopherols and tocotrienols which represent a homogeneous family of products consisting of a hydroquinone radical substituted by one or more methyl groups and a more or less saturated polyisoprene chain. The most frequently used are α-tocopherol, β-tocopherol, γ-tocopherol, α-tocotrienol. DL-α-tocopherol, a synthetic product, is the usual form of vitamin E in topical proprietary products.

Amongst the other antioxidants currently used, mention may be made of polyphenols such as resveratrol, quercetin, luteolin, gallates, certain essential oils, ascorbyl palmitate, synthetic phenolic antioxidants such as butylhydroxytoluene (BHT) and butylhydroxyanisole (BHA).

The great chemical reactivity of these antioxidants, in particular with regard to the phenolic groups thereof, renders them susceptible to oxidation, which poses problems of instability and preservation of the compositions both in terms of antioxidant activity and of the appearance of the formulations, for example the colouring or also the odour thereof. Thus it is known to protect the oxidant groups by protective groups which stabilise the active molecule during storage and are susceptible to being hydrolysed on contact with the enzymes of the skin. Although knowledge on this subject is still limited, it is generally considered that lipases, phosphatases, glucosidases, glucocerebrosidases and a sphingomyelinase are present in the *Stratum corneum* and that esterases are present in the *Stratum granulosum* of the epidermis (U. K. Jain et al, *Proceed. Intern. Symp. Control. Rel. Bioact. Mater.*, 22, (1995), Controlled Release Society, Inc., pages 702 to 703).

Thus EP-A-0 487 404 discloses the use of a glucosyl derivative of ascorbic acid in dermatological compositions. This derivative is hydrolysed by cutaneous enzymes and releases ascorbic acid when these compositions are applied to the skin. However, the use of such derivatives does not allow a sufficient quantity of ascorbic acid to be released rapidly on the surface of the skin.

EP-A-0 710 478 discloses a product for topical application containing a precursor of an active cosmetic or dermatological constituent (e.g. vitamins such as retinol, ascorbic acid) and a lipase. The precursor is an ester including at least one ester function with a linear or branched chain, saturated or unsaturated, having from 2 to 25, preferably 12 to 18 carbon atoms.

In US 2004/0202624 the authors propose conjugates which act both as antioxidants and as agents giving protection against UV radiation. A flavonoid serves as base molecule onto which is grafted one or more molecules having properties of absorption of UV radiation. More precisely, the flavonoid has radicals $R^1$ to $R^5$ which are chosen from amongst —H, —OH and —OA, where A denotes the anti-UV agent. This document uses the properties of the flavonoids for protection against the UVA rays in order to propose a conjugate having a broad spectrum of protection against UVA/B radiation. The teaching of this document encompasses numerous possibilities, concerning both the number and the nature of the anti-UV molecules to be grafted, and the possible grafting of various radicals which favour the solubility in water or in oil, and also concerning the mode of action and administration of the conjugates, between conjugates having sufficient lipophilia in order to penetrate into the deep layers of the skin, combination with transport agents such as liposomes, and systemic transport after oral administration. Certain —OH groups remaining free on the conjugate may possibly be esterified with a carboxylic acid chosen from amongst the 2-ethylhexanecarboxylic, butyric, valeric, hexanoic, ascorbic and lauric acids in order to promote the solubility in oil, and the ester radical can be hydrolysed in the cell under the effect of the esterases. On the other hand, this document does not relate to the behaviour of its different conjugates in situ in relation to the enzymes of the skin. Finally, the conjugates would have an antioxidant activity associated with the flavonoid enabling stabilisation of the formulations containing them. It is assumed that this antioxidant activity is associated with the presence of free —OH groups.

None of these teachings solves the problem of having a biologically active compound which is stable in storage but nevertheless has an antioxidant effect and/or some other biological effect on the surface of the skin and an antioxidant effect and/or some other biological effect, e.g. cosmetic or dermatological, in the lower layers under acceptable conditions of durability and effectiveness.

Another major difficulty which has not been solved by the prior teaching is to ensure at the same time that there is good penetration of the tissue if one or more active molecules are to be delivered for example into the epidermis, the dermis and/or the hypodermis, and an effective antioxidant power in the different layers of the skin, including at the surface and in the *Stratum corneum* in particular and therefore an immediate or quasi-immediate antioxidant activity on application to the skin.

Consequently there would be considerable interest in being able to have access to compositions which are stable in storage and which after application to the skin can develop a lasting activity having a powerful antioxidant action at different levels of the skin, including at the surface (protective effect from the time of application or shortly after application) and in the *Stratum corneum*, capable of penetrating into the lower layers. There would be greater interest in combining this with a biological activity of some nature or the other, for example at the level of the *Stratum corneum*, the *Stratum granulosum* and/or the lower layers of the skin, for the purposes of therapeutic treatment, in particular dermatological or cosmetic treatment.

Therefore the object of the invention is to propose molecules and compositions comprising them which enable these objects to be achieved.

These objects are achieved by a bioprecursor which complies with the structure:

in which:
PP represents a polyphenol radical in which each hydroxyl function is protected by a group A or a group B;
A is a substituted or unsubstituted, saturated or unsaturated alkyl chain comprising from 1 to 20 carbon atoms, preferably from 1 to 4, which is bound to the polyphenol by:
a carboxylic ester function on a hydroxyl function of the said polyphenol; or
by means of an A' spacer, in which A is bound to A' by a carboxylic ester function, and A' is bound to the polyphenol by a carboxylic ester function on a hydroxyl function of the said polyphenol;
n represents an integer greater than or equal to 1, in particular 1, 2, 3, 4 or 5;
B is a precursor of a biologically active molecule which is bound to the polyphenol by:
a carboxylic ester function on a hydroxyl function of the said polyphenol; or
by means of a B' spacer, in which B is bound to B' by a carboxylic ester function, and B' is bound to the polyphenol by a carboxylic ester function on a hydroxyl function of the said polyphenol;
m represents an integer greater than or equal to 1, in particular 1 or 2.

It should be understood that when n is greater than 1, the protective groups A may be identical or different. Equally, when m is greater than 1, the B precursors may be identical or different. The B precursor(s), which like the A groups protect the hydroxyl functions of the polyphenol, are different from the said A groups in that they also give the bioprecursor according to the invention a therapeutic activity, in particular a dermatological or cosmetic activity.

The bioprecursor is capable of being biohydrolysed under the action of skin enzyme(s) in order to restore the hydroxyl functions and to release the said polyphenol and the said biologically active molecule, present in the form of its B precursor in the bioprecursor. Thus the bioprecursors according to the invention comprising a polyphenol and at least one biologically active B molecule precursor are known as "multifunctional bioprecursors".

It appears in a quite surprising manner that the bioprecursor according to the invention enables the controlled and progressive release of biologically active compounds and in particular in the different layers of the skin. This makes it possible in particular to improve the bioavailability of the biologically active compounds which are conveyed in the form of a bioprecursor compound. In fact it appears that certain hydroxyl functions of the polyphenol molecule may be released even though the bioprecursor is located in the upper parts of the skin, such as the *Stratum corneum*, in particular under the action of lipases. This enables the polyphenol to recover its antioxidant activity. Thus the bioprecursor can exhibit an antioxidant activity from the moment of its contact with the skin and during the entire passage through the epidermis, in particular through the *Stratum corneum*. The other hydroxyl functions of the polyphenol molecule can also be released when the bioprecursor penetrates into the live tissue, in the region of the lower or deep parts of the skin, such as the *Stratum granulosum*, in particular under the action of the esterases. This enables the complete release of the polyphenol and of the biologically active B molecules. Considerations concerning the physiology of the cutaneous absorption are mentioned in Agache et al, *Encyclopédie Médico-Chirurgicale* (Paris) 12-235-C-30, (1995).

In an advantageous manner the protective groups of the polyphenol can be released solely when the bioprecursor according to the invention is placed in conditions where the biologically active molecules should act, which makes it possible to exploit their properties in an optimal manner. The progressive release of biologically active compounds of the bioprecursor also makes it possible to avoid the local over-concentrations and the effects of accumulations of the active molecules, which can cause irritations of the skin.

The bioprecursor according to the invention exhibits in particular a very good cutaneous penetration.

The polyphenol can also be used as a transcutaneous vector intended to release a pharmaceutically active constituent and to render it bioavailable for applications other than dermatological ones. In particular, the pharmaceutically active constituent which is released is then intended to be conveyed by the blood.

The bioprecursor according to the present invention also has the advantage of being perfectly stable in a cosmetic, dermatological or other therapeutic formulation, and of not exhibiting any problem of compatibility with the excipients and/or additives generally used in the said formulations.

The protective groups A stabilise the bioprecursor during storage thereof but are easily hydrolysed by the enzymes of the skin, and the hydrolysis starts shortly after contact with the latter, which enables the bioprecursor rapidly to develop the antioxidant properties of the polyphenol and the biologically active properties of the molecule B. Moreover, the groups A make it possible to adjust the kinetics of biohydrolysis of the bioprecursor and thus release of the active compounds.

A is advantageously derived from a linear, branched or cyclic carboxylic acid, for example chosen from amongst ethanoic acid, propanoic acid, linear or branched butanoic acid, caproic acid and lauric acid.

The expression "biologically active molecule" is understood to mean molecules of natural, artificial, synthetic origin or derived from biotechnologies, which are biologically effective. Thus within the cosmetics field, a biologically active molecule is effective on the skin via biological targets in order to provide beneficial effects for the skin, for example to combat drying, ageing or pigmentation of the skin, or to promote the restructuring of the skin or skin cell renewal.

A precursor B is understood to be a radical capable of being released by enzymatic hydrolysis in the form of a biologically active molecule.

When the invention relates to a therapeutic, dermatological or other application, the biologically active molecule is a pharmaceutically active constituent and the precursor B is chosen as a consequence.

The biologically active molecule may be chosen from amongst: an astringent molecule, an antioxidant molecule, an anti-free radical, anti-lipoperoxidant and/or anti-wrinkle molecule, a restructuring or biostimulating molecule, a photoprotective agent, such as an anti-UV molecule, a self-tanning agent, a moisturising molecule, a cooling or warming molecule, a bleaching and/or anti-blemish molecule, a slimming molecule, a molecule for stimulating microcirculation and/or protecting the vascular system, a tanning activator, a glycation inhibitor, an immunostimulating molecule, an anti-inflammatory and/or anti-irritant agent, a cooling molecule, a warming molecule, a flavouring molecule or a fragrancing molecule, etc.

According to a preferred embodiment, the biologically active molecule may be chosen from amongst: an antioxidant molecule, an anti-free radicals molecule, a tanning activator, a bleaching and/or anti-blemish molecule, a self-tanning agent, a photoprotective agent, an anti-UV molecule.

According to preferred variants of the invention, the biological molecule is chosen from amongst: polyphenol, lipoic acid, vitamins A, B, D, E, F, unsaturated or polyunsaturated organic acids, retinoic acids, hydroxyacids, polyols.

Without wishing to be exhaustive, but in order to give a more complete overview of the biological functions which may benefit from the invention, in particular in cosmetics and dermatology, and of the molecules which may be associated therewith, mention may be made of:

astringent agents, such as tannins;

moisturising agents, in particular agents which control cutaneous perspiration such as saccharides (glucose, sorbitol, hyaluronic acid), but also glycerol and α-hydroxyl acids, ceramides of plant origin which are moisturising through their polar part, hydroxyacids, in particular lactic acid; agents for stimulation of epidermal differentiation; agents which promote lipid synthesis;

antioxidant, anti-free radical, anti-lipoperoxidant and/or anti-wrinkle agents: inhibitors of free radicals are essential for the prevention and treatment of the degradation of lipids, proteins and DNA under the action of the radicals as well as the other damage to the biomolecules of the skin surface, damage which leads to the formation of wrinkles. Non-limiting examples: tocopherols (vitamin E, tocol, α-tocopherol, γ-tocopherol, δ-tocopherol), carotenoids (lutein, zeaxanthine), diterpenoids and triterpenoids (e.g. carnosol, oleuropeine), flavonoids (e.g. luteolin, epigallocatechin gallate), ascorbic acid, stilbenoids (e.g. resveratrol), tannins, phenolic acids (e.g. chlorogenic acid, salicylic acid), retinoids (e.g. vitamin A, retinol, retinylpalmitate), lipoic acid, hydroxycoumarins (e.g. aminoresorcinol, aesculetine), aurones (e.g. aureusin), chalcones, hydroxyamino acids (e.g. tryptophan, tyrosine, hydroxytyrosine), alkylphenols (e.g. cardol);

restructuring or biostimulating agents (leading to an anti-wrinkle, anti-ageing effect): agents stimulating the synthesis of the elements of the extracellular matrix (MEC), more precisely inhibiting the enzymes which degrade collagen (e.g. collagenases) and stimulating the glucosaminoglycans which increase the collagen content and therefore increase the elasticity of the skin (examples: vitamin C, vitamin A, peptides); agents for protection of the MEC, anti-metalloproteinase action of MMP matrix (activity and synthesis) and/or stimulating of the tissue inhibitor of metalloproteinase TIMP (example: luteolin, vitamin A);

slimming agents: for example caffeine;

agents for stimulation of the microcirculation and/or vasculoprotective agents, such as vitamin P factors; examples: flavonoids, such as rutin, rutoside;

tanning activators, such as plant extracts and the peptides responsible for stimulating melanogenesis; example of peptide: acetyl-hexapeptide-1;

bleaching and/or anti-blemish agents: acting by reducing the melanogenesis; example: resveratrol, vitamin C and derivatives thereof;

self-tanning agents, in particular agents for cutaneous surface pigmentation such as DHA (dihydroxyacetone);

glycation inhibiting agents, for example resveratrol, α-lipoic acid;

immunostimulating agents, for example: β-glucan, lentinan, deepsane;

photoprotective agents, for example methoxycinnamates, for example octyl-methoxycinnamate, octocrylene, hydroxybenzophenones, photoprotective salicylates, such as methyl or octyl salicylate;

anti-inflammatory and/or anti-irritant agents, for example resveratrol, THC, luteolin;

fragrancing agents, such as vanillin, vanillate;

cooling agents, such as menthol;

warming agents, such as vanillylbutyl ether.

In particular the biologically active B molecules and polyphenol may be chosen in order to obtain the different combined, conjugate or synergistic cosmetic or dermatological effects.

Amongst the therapeutic molecules mention may be made of the steroid hormones produced in the cortex by the adrenal gland, such as for example cortisol and aldosterone. These two hormones regulate the metabolism of glucose and the excretion of salt. Mention may also be made of anti-inflammatory and anti-asthma agents, such as prednisolone and prednisone.

When the B precursor includes one or more OH alcohol functions, they can be protected in particular by a hydrocarbon protective group, which may be of the same type as A, by means of a carboxylic ester function. Amongst the B precursors including several OH functions, the precursors of gallic acid and derivatives thereof are not preferred; advantageously B is not a precursor of the gallic acid or of one of the derivatives thereof.

The large families of polyphenols which may be used are the following:

Stilbenoids: for example resveratrol;

Flavonoids:
  The families comprising flavonol, flavone, isoflavone, flavanone, anthocyanidins, flavanol, flavillium;
  Examples: quercetin, luteolin, catechin, epigallocatechin;

Tannins:
  Hydrolysable tannins: gallic and ellagic acid polyesters;
  Condensed tannins: proanthocyanidols;
  Phlorotannins: e.g. fucofuroeckol;

Phenylpropanoids: e.g. curcumin, caffeic acid and derivatives thereof, and in particular esters thereof, e.g. [[(2E)-3-(3,4-dihydroxyphenyl)-1-oxo-2-propenyl]oxy]-3,4-dihydroxybenzenepropanoic acid (rosmarinic acid);

Diarylheptanoids: curcuminoids: for example tetrahydrocurcumin;

Aurones (e.g. aureusin);

Alkylpolyphenols (e.g. cardol);

Dihydrochalcones;

Dihydroxycoumarins;

Polyhydroxyphenylamino acids (e.g. hydroxytyrosine) or polyhydroxyphenylamino alcohols (e.g. adrenaline);

Anthracenone (e.g. aloin);

Benzenediols, benzenetriols (e.g. pyrogallol);

Glycosyl polyphenols: e.g. hesperidine, diosmine;

In the sense of the invention polyphenol is understood to mean a molecule comprising at least one aromatic ring of the benzene type, possibly comprising one or more heteroatoms, and at least 2 OH alcohol functions. The aromatic rings can comprise no, one or more OH alcohol functions. According to a characteristic according to the invention, the polyphenol is of the type having at least 2 phenol nuclei.

Thus it may for example comply with the following formula:

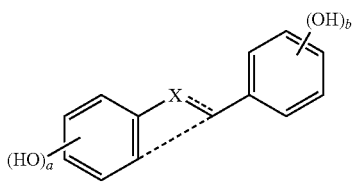

in that:
a is 1, 2, 3, 4 or 5;
b is 1, 2, 3, 4 or 5;
X is N, S, O, CH, $CH_2$, CO, NH;
- - - - represents a double or a single bond;
- - - - represents a chain which may be present, forming a ring with 5 or 6 links, including X and having one or more double bonds, possibly one or more OH substituents and/or one or more heteroatoms chosen from amongst N, S, O, which are situated in the ring and/or substitute therefor.

The polyphenol may in particular also comply with the following formula:

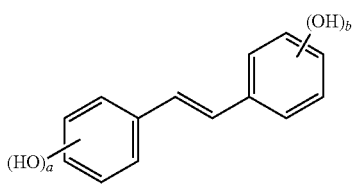

in which a is 1, 2, 3, 4 or 5 and b is 1, 2, 3, 4 or 5, and preferably a is 2 and b is 1.

The polyphenol may also comply with the following formula:

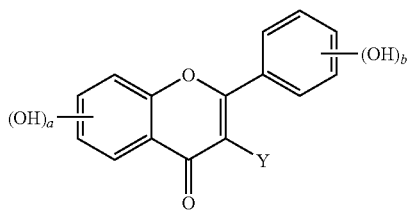

in which Y is H or OH, a is 1, 2, 3, or 4 and b is 1, 2, 3, 4 or 5, and preferably, a is 2 and b is 2.

Preferred examples of polyphenols are: resveratrol, luteolin, quercetin, hydroquinone, pyrocatechol, gallic acid, hydroxytyrosol, tetrahydrocurcumin, silymarin, ellagic acid.

When they are present, the A' and B' spacers may be, independently of one another, a preferably aliphatic hydrocarbon chain comprising at least two acid functions (in particular of the diacid type) or at least one acid function and at least one hydroxyl function (in particular of the hydroxyacid type) comprising from 2 to 13 carbon atoms, preferably 2 to 5. These spacers can also have other hydroxyl, acid or anine functions. A spacer is understood in particular to be a molecule which makes it possible to bind, by ester functions, two molecules having hydroxyl functions. The spacer may also have an additional biological effect, such as for example a moisturising effect for a hydroxyacid.

A' and B' are preferably independently of one another a succinic acid, adipic acid, brassylic acid, lactic acid, salicylic acid, 4-hydroxybenzoic acid, ferulic acid, tartaric acid, 2-hydroxybutanoic acid, 3-hydroxybutanoic acid or 4-hydroxybutanoic acid radical.

The present invention relates in particular to one of the following bioprecursors:

(E)-4-(3,5-diacetoxystyryl)phenyl-5-(1,2-dithiolan-3-yl)pentanoate (or 3,5-resveratrol diacetate-4'-lipoate=Res(Ac)-2-Lipoate);

(E)-4-(3,5-diacetoxystyryl)phenyl-2,5,7,8-tetramethyl-2-(4,8,12-trimethyltridecyl)-3,4-dihydro-2H-chromen-6-yl succinate (or 3,5-resveratrol diacetate-4'-succinyltocopheryl=Res(Ac)$_2$-succinate-Vit E);

4-[(E)-3,5-diacetoxystyryl]phenyl-(2Z,4E,6Z,8E)-3,7-dimethyl-9-(2,6,6-trimethylcyclohex-1-enyl)nona-2,4,6,8-tetraenyl succinate (or 3,5-resveratrol diacetate-4'-succinylretinyl=Res(Ac)-2-succinate-Vit A);

(2E,4E,6E,8E,10E,12E)-4-[(E)-3,5-diacetoxystyryl]phenyl-docosa-2,4,6,8,10,12-hexaenoate (or 3,5-resveratrol diacetate-4'-docosahexanoate, derivative of mono-omega-3);

(E)-4-(3,5-diacetoxystyryl)phenyl-4-hydroxy-3-methoxybenzoate (or 3,5-resveratrol diacetate-4'-vanillate);

(E)-4-(3,5-diacetoxystyryl)phenyl-3,4-diacetoxybenzoate (or 3,5-resveratrol diacetate-4'-(3,4-diacetoxy)benzoate);

(E)-4-[(E)-3,5-diacetoxystyryl]phenyl-3-(4-hydroxy-3-methoxyphenyl)acrylate (or 3,5-resveratrol diacetate-4'-ferulate);

(E)-4-[(E)-3,5-diacetoxystyryl]phenyl-3-(4-acetoxy-3-methoxyphenyl)acrylate (or 3,5-resveratrol diacetate-4'-acetylferulate);

(E)-4-[(E)-3,5-diacetoxystyryl]phenyl-3-(4-methoxyphenyl)acrylate (or 3,5-resveratrol diacetate-4'-(4-methoxy)cinnamate);

(E)-4-(3,5-diacetoxystyryl)phenyl-2-acetoxybenzoate (or 3,5-resveratrol diacetate-4'-acetylsalycilate);

7-acetoxy-2-(3,4-diacetoxyphenyl)-4-oxo-4H-chromen-5-yl-5-(1,2-dithiolan-3-yl)pentanoate (or luteolin triacetate-lipoate);

7-acetoxy-2-(3,4-diacetoxyphenyl)-4-oxo-4H-chromen-5-yl-2,5,7,8-tetramethyl-2-(4,8,12-trimethyltridecyl)-3,4-dihydro-2H-chromen-6-yl succinate (or luteolin triacetate-monosuccinyltocopheryl);

2-methoxy-4-(7-(3-methoxy-4-(prop-1-en-2-yloxy)phenyl)-3,5-dioxoheptyl)phenyl-5-(1,2-dithiolan-3-yl)pentanoate (or tetrahydrocurcumin monoacetate-monolipoate);

2-methoxy-4-(7-(3-methoxy-4-(prop-1-en-2-yloxy)phenyl)-3,5-dioxoheptyl)phenyl-2,5,7,8-tetramethyl-2-(4,8,12-trimethyltridecyl)-3,4-dihydro-2H-chromen-6-yl succinate (or tetrahydrocurcumin monoacetate-monosuccinyltocopheryl).

Amongst the bioprecursors defined above, those which are preferred are in particular of (E)-4-(3,5-diacetoxystyryl)phenyl-5-(1,2-dithiolan-3-yl)pentanoate (or 3,5-resveratrol diacetate-4'-lipoate Res(Ac)-2-Lipoate) and (E)-4-(3,5-diacetoxystyryl)phenyl-2,5,7,8-tetramethyl-2-(4,8,12-trimethyltridecyl)-3,4-dihydro-2H-chromen-6-yl succinate (or 3,5-resveratrol diacetate-4'-succinyltocopheryl=Res(Ac)$_2$-succinate-Vit E).

In general, the invention relates to the application of the bioprecursors described above in the therapeutic field, for example the dermatological, or cosmetic field.

The present invention also relates to compositions containing at least one bioprecursor according to the invention, in a topical formulation which is acceptable for the envisaged therapeutic, dermatological or cosmetic application. The invention also relates to the use of a bioprecursor as defined above for the preparation of a therapeutic, dermatological or cosmetic composition.

By way of examples, and in non-limiting manner, the compositions containing at least one bioprecursor according to the invention may be personal care compositions for the face or for the body, personal care compositions for slimming, sun-screening compositions, fragranced compositions, makeup compositions, such as foundations or powders, compositions for the lips in the form of balms, of lipsticks or gloss, or mascara compositions, body hygiene compositions, such as shower gels or deodorants.

The acceptable medium generally comprises water, and/or a mixture of water and of fatty substances, and/or a mixture of fatty substances, and/or a mixture of water and of silicone. The technical field offers a wide choice of types of topical formulations, and mention may be made, without wishing to be exhaustive, of: emulsions (e.g. O/W, W/O, W/O/W, O/W/O, W/Si; W=water, O=oil, Si=silicone), suspension, solution, paste, ointment, aqueous gel, hydro-alcoholic gel, cream, lotion, powder, soap, spray, mousse.

These compositions may also contain acceptable cosmetic or dermatological additives. These additives may be in particular, but in a non-limiting manner, surfactants, fatty substances, such as oils, active free molecules, such as moisturisers or hydrophilic or lipophilic active constituents, preservatives, fragrances, chelating agents, pigments, filters, sequestering agents, colouring materials, fillers, humectants, thickeners, such as gelling agents, texturing agents, flavourings, solvents etc.

In a non-limiting manner, the following additives may be used in the compositions according to the present invention:
- oils, chosen in particular from amongst: linear or cyclic, volatile or non-volatile silicone oils such as polydimethylsiloxanes (dimethicones), polyalkylcyclosiloxanes (cyclomethicones) and polyalkylphenylsiloxanes (phenyldimethicones); synthetic oils such as fluorinated oils, alkylbenzoates and branched hydrocarbons such as polyisobutylene; vegetable oils and in particular soya or jojoba oils; and mineral oils such as paraffin oil;
- waxes, such as ozokerite, polyethylene wax, beeswax or carnauba wax;
- silicone elastomers obtained in particular by reaction, in the presence of a catalyst, of a polysiloxane having at least one reactive group (hydrogen or vinyl, in particular) and having at least one terminal and/or lateral alkyl (in particular methyl) or phenyl group, with an organosilicone such as an organohydrogenopolysiloxane;
- surfactants, preferably emulsifiers, which may be non-ionic, anionic, cationic or amphoteric, and in particular esters of fatty acids and polyols such as esters of fatty acids and of glycerol, esters of fatty acids and of sorbitan, esters of fatty acids and of polyethyleneglycol and esters of fatty acids and of sucrose; ethers of fatty alcohols and of polyethyleneglycol; alkylpolyglucosides; polysiloxane modified polyethers; betaine and derivatives thereof; polyquaterniums; ethoxylated fatty alcohol sulphate salts; sulfosuccinates; sarcosinates; alkyl and dialkyl phosphates and salts thereof; and fatty acid soaps;
- co-surfactants such as linear fatty alcohols and in particular cetyl and stearyl alcohols;
- thickeners and/or gelling agents, and in particular hydrophilic or amphiphilic homo- and copolymers, cross-linked or not, of acryloylmethylpropane sulphonic acid (AMPS) and/or of acrylamide and/or of acrylic acid and/or of acrylic acid salts or esters; xanthan or guar gum; cellulose derivatives; and silicone gums (dimethiconol);
- humectants, such as polyols, including glycerine, propylene glycol and sugars, and glycosaminoglycans such as hyaluronic acid and salts and esters thereof;
- organic filters, such as derivatives of dibenzoylmethane (including butyl-methoxydibenzoylmethane), derivatives of cinnamic acid (including ethylhexyl-methoxycinnamate), salicylates, para-aminobenzoic acids, β-β'-diphenylacrylates, benzophenones, the derivatives of benzylidene camphor, phenylbenzimidazoles, triazines, phenylbenzotriazoles and anthranilic derivatives;
- inorganic filters, based on mineral oxides in the form of pigments or of nanopigments, coated or uncoated, and in particular based on titanium dioxide or zinc oxide;
- colourings;
- preservatives;
- fillers, and in particular powders with a "soft-focus" effect, which may in particular be chosen from amongst polyamides, silicon, talc, mica, fibres (in particular of polyamide or of cellulose);
- sequestering agents such as EDTA salts;
- fragrances;

and mixtures thereof, without this list being limiting.

Examples of such additives are cited in particular in the CTFA Dictionary (*International Cosmetic Ingredient Dictionary and Handbook*, published by *The Cosmetic, Toiletry and Fragrance Association*, 9$^{th}$ Edition, 2002).

Naturally the person skilled in the art will take care to choose this or these possible additives in such a way that the advantageous properties intrinsically associated with the composition according to the invention are not, or not substantially, altered by the envisaged addition(s).

The bioprecursors and compositions according to the invention are advantageously insensitive or only a little sensitive to external factors such as light or heat, variations of pH and additives such as surfactants, solvents, metal catalysts. This stability makes it possible to retain the required effectiveness and the visual appearance and the odour of the compositions.

The quantities of the different constituents of the compositions are those which are conventionally used in the relevant field, e.g. cosmetic and dermatological.

The quantity of bioprecursor in the compostions according to the invention depends upon numerous factors, amongst which mention may be made, in a non-limiting manner, of the type of formulation, the nature of the bioprecursor, the mode of administration, the severity of any pathology to be treated, the intensity of the desired effect, and others. The quantity of bioprecursor may for example be comprised between 0.001% and 20%, preferably between 0.005% and 15%, even more preferably between 0.01% and 10%, advantageously between 0.05% and 5%, or even between approximately 0.08% and approximately 2%.

The present invention also relates to the use of a polyphenol as described here, in particular comprising all or some of its hydroxyl functions protected by the A groups, as a vector which makes it possible to make one or more biologically active molecules, such as those described here, penetrate into the skin, and more particularly in one or more of the layers of the skin.

The bioprecursors according to the invention may be manufactured by different processes known from the prior art, such as processes of acylation of derivatives of phenols (see *Protective Groups in Organic Synthesis*, T. W. Green, second edition, (1991), page 162), of the processes of selective deprotection of phenol esters using enzymatic systems.

The present invention relates in particular to a process for manufacture of bioprecursors according to the invention comprising at least the following steps:

a) protection of the polyphenol by peresterification, such as peracetylation, by a compound A-Z, Z being a function capable of reacting with an OH function of the polyphenol in order to generate the ester bond between the polyphenol and A, b) selective deprotection in such a way as to obtain one or more free OH functions of the polyphenol, and c) coupling of the intermediate obtained after the step b) with the biologically active B molecule previously activated.

In so far as the step a) is concerned, peracetates may be prepared by peracetylation of resveratrol under standard conditions in the presence of pyridine and an excess of acetic anhydride as described by H. Aft in *Journal of Organic Chemistry*, 26, (1961), 1958-1963. The reaction is carried out by heating to 80° C. for several hours. The synthesis is conventional and leads to the desired product with very good yields.

In so far as the selective deprotection of step b) is concerned, the selective de-esterification, e.g. de-acetylation, of a peresterified, e.g. peracetylated, compound may be carried out with the aid of an enzyme, such as for example a microbial lipase, as described by Nicolosi et al in *Journal of Molecular Catalysis B: Enzymatic*, 16, (2002), 223-229. The enzyme used is for example the lipase of *Candida antarctica* immobilised on a polypropylene resin. The lipase is marketed by Novo Nordisk under the name Novozym SP4350.

The de-esterification or the de-acetylation catalysed by the lipase may be carried out either by a hydrolysis reaction in an aqueous medium or by alcoholysis in an organic solvent. Most often an "alcohol" medium is used and alcoholysis is referred to. The reaction is carried out in under "gentle" conditions of temperature (15 to 75° C.) and of pH (5-8, if it is an aqueous medium).

The product is generally obtained by simple filtration of the enzyme and by concentration under reduced pressure of the reaction medium.

In step c), the coupling of the intermediate obtained after step b) with the previously activated biologically active B molecule may be carried out by a method of coupling known to the person skilled in the art (DCC=dicyclocarbodiimide, chlorination of an acid function in acid chloride, etc.).

Chlorination with thionyl chloride is the method most used because the products formed are easily obtained and used without isolation (see J. S. Pizey, Synthetic Reagents, 1, (1974), 321). The reaction is carried out at ambient temperature in one of the anhydrous solvents such as dichloromethane.

The coupling between an alcohol and an acid may be catalysed by a dehydration agent such as for example dicyclohexylcarbodiimide (DCC). The reaction conditions are described by M. Smith et al in *J. Am. Chem. Soc.*, 80, (1958), 6204.

The present invention also relates to a process for cosmetic treatment of the skin consisting of applying to the said skin a composition such as that described previously, of which the bioprecursor contains a B precursor of a compound which is active in the cosmetic field. The invention relates in particular to a cosmetic process of release of polyphenol and active B molecules at the level of the *Stratum corneum* or of the living tissue of the skin by topical application to the skin of a composition as defined above.

The invention also relates to a process of dermatological treatment consisting of applying to the skin a composition as previously described, the bioprecursor of which contains a B precursor of a compound which is active from the dermatological point of view.

The invention also relates to a process of therapeutic treatment consisting of applying to the skin a composition as described previously, the bioprecursor of which contains a B precursor of a pharmaceutical compound to be delivered transcutaneously, in particular with a systemic action.

The invention will now be described with the aid of embodiments given by way of non-limiting examples.

EXAMPLE 1

Synthesis of (E)-4-(3,5-diacetoxystyryl)phenyl-5-(1, 2-dithiolan-3-yl)pentanoate (3,5-resveratrol diacetate-4'-lipoate=Res(Ac)$_2$-Lipoate)

The mixed ester 3,5-diacetyl-4'-lipoyl resveratrol (1) is obtained in four steps by esterification of resveratrol diacetate with lipoyl chloride in the presence of triethylamine and DMAP (dimethylaminopyridine) in tetrahydrofuran (THF) at 0° C.

a) Preparation of 3,5,4'-resveratrol triacetate(Res(AC)$_3$)

Pyridine (10 eq) is added dropwise whilst stirring at ambient temperature to a solution of resveratrol (156 g with a purity of 96%, 0.66 mole) in acetic anhydride (372 ml, 6 eq). The reaction medium is heated to 80° C. for 1 hour. The product is obtained after precipitation in 3 l of water, filtration and two successive washings with water. Resveratrol triacetate is obtained with a quantitative yield and a HPLC purity of 99% (300 nm) and molar purity measured by NMR of the proton of 98%.

Melting point=120-121° C.

NMR $^1$H (DMSO/HMDS; 300 MHz): 2.21 (s, 3H); 2.23 (s, 6H); 6.85 (t, 2.2 Hz, 1H); 7.10 (d, 8.5 Hz, 2H); 7.15 (d, 16.5 Hz, 1H); 7.23 (d, 2.2 Hz, 2H); 7.28 (d, 16.5 Hz, 1H); 7.57 (d, 8.5 Hz, 2H).

b) Synthesis of 3,5-resveratrol diacetate(Res(Ac)$_2$)

Resveratrol diacetate is obtained by enzymatic alcoholysis of resveratrol triacetate (1.1) with Novozyme® SP435 as described by Nicolosi et al (*Journal of Molecular Catalysis B: Enzymatic*, 16, (2002), 223-229) with certain modifications, namely: tert-butylmethylether (TBME) was replaced by acetonitrile and the quantity of enzyme was decreased to 20% p/p. The alcoholysis of the resveratrol triacetate is carried out on the scale of 200 g/l of resveratrol triacetate with n-butanol in the presence of 20% p/p of Novozyme SP435 in acetonitrile at 65° C. and in 15 hours. The crude product is obtained by filtration of the enzyme and by concentration of the reaction medium under reduced pressure. The crude product is a mixture of 88% diacetate (1.2) and 12% monoacetate. It was purified by chromatography on a column of silica with cyclohexane/ethyl acetate (4/1 v/v) as eluent. The pure product is obtained with a yield of 50% and a molar purity measured by NMR of the proton of 99%.

Melting point=134-136° C.

NMR $^1$H (DMSO/HMDS; 300 MHz): 2.22 (s, 6H); 6.72 (d, 8.5 Hz, 2H); 6.78 (t, 2.2 Hz, 1H); 6.93 (d, 16.2 Hz, 1H); 7.15 (d, 16.2 Hz, 1H); 7.16 (d, 2.2 Hz, 2H); 7.36 (d, 8.5 Hz, 2H); 9.58 (br s, OH).

c) Synthesis of 3,5-resveratrol diacetate-4'-lipoate (Res(Ac)-2-Lipoate)

The synthesis of lipoic acid chloride (DL-thioctic acid) was carried out under argon at ambient temperature following a standard protocol: lipoic acid (5 g, 24 mmol) is solubilised in dichloromethane (40 ml) and $SOCl_2$ (1.3 eq) is added dropwise. After 1 hour of stirring at ambient temperature, the lipoic acid chloride formed is poured onto a solution of resveratrol diacetate (1.2) (6 g, 19 mmol) in THF (100 ml), containing triethylamine (3 eq) and DMAP (0.45 eq). After 1 hour the reaction mixture is diluted with 100 ml $CH_2Cl_2$, then washed with two times 90 ml of HCl 5% v/v. The organic phase is dried over anhydrous $MgSO_4$, filtered, then concentrated in a rotary evaporator. The crude product (11.4 g) is purified by chromatography on a column of silica with cyclohexane/ethyl acetate (4/1 v/v) as eluent. The fractions containing the pure product are evaporated to lead to 5.95 g of 3,5-resveratrol diacetate-4'-lipoate 1 (49% of yield) with a molar purity measured by NMR of the proton of 96%.

Melting point=79-81° C.

NMR $^1$H (DMSO/HMDS; 300 MHz): 1.42 (m, 2H); 1.60 (m, 4H); 1.84 (m, 1H); 2.23 (s, 6H); 2.36 (m, 1H); 2.53 (t, 7.4 Hz, 2H); 3.09 (m, 2H); 3.54 (m, 1H); 6.85 (t, 2.2 Hz, 1H); 7.08 (d, 8.5 Hz, 2H); 7.15 (d, 16.7 Hz, 1H); 7.23 (d, 2.2 Hz, 2H); 7.28 (d, 16.7 Hz, 1H); 7.58 (d, 85 Hz, 2H).

EXAMPLE 2

Synthesis of (E)-4-((E)-3,5-diacetoxystyryl)phenyl 3-(4-acetoxy-3-methoxyphenyl)acrylate (3,5-resveratrol diacetate-4'-acetylferulate)

The mixed ester 3,5-resveratrol diacetate-4'-acetylferulate is obtained in five steps by esterification of resveratrol diacetate with O-acetyl ferulic acid chloride in the presence of triethylamine and of DMAP in THF at 0° C.

a) Synthesis of (E)-3-(4-acetoxy-3-methoxyphenyl) acrylic acid (O-acetyl ferulic acid)

Ferulic acid (10 g, 51 mmol) is solubilised in 100 ml of anhydrous THF under argon. Triethylamine (8.7 ml, 61 mmol, 1.2 eq) is added quickly, then DMAP (3.34 g, 27 mmol, 0.5 eq) at ambient temperature and under argon. Finally acetic anhydride (5.9 mL, 61 mmol, 1.2 eq) is added in 3 min, at ambient temperature. This is kept whilst stirring, at ambient temperature, for 18 h, then the medium is transferred into a separation funnel. This medium is diluted with 100 ml of THF, acidified with 40 ml of HCl 5% v/v and the organic phase is washed with 5×40 ml of $H_2O$. The final organic phase is dried over $MgSO_4$, filtered, then evaporated dry in a rotary evaporator (40° C., 30 mbar). 9.5 g of a crude yellow solid are obtained with a crude yield of 79% and a molar purity measured by NMR of 86%. The product is involved in the following step without purification.

b) (E)-4-(3-chloro-3-oxoprop-1-enyl)-2-methoxyphenyl acetate(O-acetyl ferulic acid chloride)

DMF (200 μl, 26 mmol), then thionyl chloride (2.35 ml, 32 mmol, 1.2 eq) are added to a suspension of O-acetyl ferulic acid (6.24 g, 26 mmol) in 30 ml of chloroform, at ambient temperature. The medium is heated to reflux for 4 h, then it is allowed to return to ambient temperature and the medium is evaporated dry in a rotary evaporator. A yellow solid is obtained with a quantitative crude yield. The product is involved in the following step without purification.

c) (E)-4-[(E)-3,5-diacetoxystyryl]phenyl 3-(4-acetoxy-3-methoxyphenyl)acrylate (3,5-resveratrol diacetate-4'-acetylferulate)

Resveratrol diacetate (1.92 g, 5 mmol) is added and solubilised in 10 ml of anhydrous THF. Triethylamine (2.15 ml, 15 mmol, 3 eq) is added quickly, then DMAP (121 mg, 1 mmol, 0.2 eq). A solution of O-acetyl ferulic acid chloride (1.27 g, 5 mmol, 1 eq) solubilised in 10 ml of anhydrous THF+3 ml of dichloromethane is added at ambient temperature. After 4 h of stirring at ambient temperature, the medium is transferred into a separation funnel, diluted with 50 ml of dichloromethane and acidified with HCl 5% v/v. The organic phase is washed with 20 ml of saturated aqueous $NaHCO_3$, then with 4×30 ml of $H_2O$. The final organic phase is dried over $MgSO_4$, filtered and evaporated dry in a rotary evaporator. 2.84 g of crude solid with a quantitative yield are obtained. The crude product is solubilised in dichloromethane, then precipitated with pentane. The final product is isolated with a yield of 50% and a molar purity of 76% and 24% of the starting resveratrol diacetate.

NMR$^1$H(CDCl$_3$, HMDS, 300 MHz): 2.22 (s, 9H); 3.79 (s, 3H); 6.50 (d, 15.9 Hz, 1H); 7.09 (d, 8.5 Hz, 2H); 7.43 (d, 8.5 Hz, 2H); 7.75 (d, 15.9 Hz, 2H).

EXAMPLE 3

Synthesis of (E)-4-(3,5-diacetoxystyryl)phenyl-2,5,7,8-tetramethyl-2-(4,8,12-trimethyltridecyl)-3,4-dihydro-2H-chromen-6-yl succinate (3,5-resveratrol diacetate-4'-monosuccinyltocophryle=Res(Ac)$_2$-succinyl-Vit E)

The mixed ester 3,5-diacetate-4'-succinyltocopherol is obtained in three steps by esterification of resveratrol diacetate with tocopherylsuccinate chloride in the presence of triethylamine and of DMAP in THF at 0° C.

a) Synthesis of 4-oxo-4-(2,5,7,8-tetramethyl-2-(4,8,12-trimethyltridecyl)-3,4-dihydro-2H-chromen-6-yloxy)butanoic acid (vitamin E succinate)

Racemic α-tocopherol (10.2 g, 23 mmol) and succinic anhydride (1.5 eq) are dissolved in 50 ml of dichloromethane. DMAP (0.5 eq) and triehylamine (1.05 eq) are added and the reaction is followed by thin layer chromatography (TLC) (ethyl acetate/cyclohexane 50/50 v/v). The reaction mixture is stirred overnight at ambient temperature and shielded from the light. The mixture is diluted with 40 mL of dichloromethane, washed with HCl 5% v/v, then with $H_2O$ and the organic phase is dried over $MgSO_4$, then evaporated dry in a rotary evaporator. The crude product is obtained with a quantitative yield. This crude product is solubilised in diethyl ether and this solution is filtered through a silica cake. The filtrate obtained is evaporated dry in a rotary evaporator. An oil is obtained which solidifies at 4° C. The product is isolated with a yield of 70% and a molar purity of 94% (measured by NMR $^{13}$C).

NMR$^{13}$C(CDCl$_3$, TMS, 75 MHz): 11.7 (CH$_3$Ph); 11.9 (CH$_3$Ph); 12.8 (CH$_3$Ph); 19.6 (2CH$_3$ chain); 20.5 (CH$_2$ ring); 21.0 (CH$_2$ chain); 22.5 (CH$_3$ chain); 22.6 (CH$_3$ chain); 23.8 (CH$_3$ ring); 24.4 (CH$_2$ chain); 24.7 (CH$_2$ chain); 27.9 (CH chain); 28.5 (CH$_2$C=O); 28.9 (CH$_2$C=O); 31.0 (CH$_2$ ring); 32.7 (CH chain); 32.7 (CH chain); 37.5 (4 CH$_2$ chain); 39.3

(CH$_2$ chain); 39.9 (CH$_2$ chain); 75.0; Q ring); 117.3 (Q arom); 123.0 (Q arom); 124.8 (Q arom); 126.7 (Q arom); 140.4 (Q arom); 149.4 (Q arom); 170.7 (COOPh); 177.8 (COOH).

b) Synthesis of 2,5,7,8-tetramethyl-2-(4,8,12-trimethyltridecyl)-3,4-dihydro-2H-chromen-6-yl-chloro-4-oxobutanoate (vitamin E succinate chloride)

The synthesis of tocopherylsuccinate chloride was carried out under argon at ambient temperature following a standard protocol (a slight excess of SOCl$_2$, triethylamine, dichloromethane) at ambient temperature and under argon. The acid chloride is not isolated and is involved as it is in the following step of esterification.

c) Synthesis of (E)-4-(3,5-diacetoxystyryl)phenyl-2,5,7,8-tetramethyl-2-(4,8,12-trimethyltridecyl)-3,4-dihydro-2H-chromen-6-yl succinate (3,5-resveratrol diacetate-4'-succinyltocopheryl=Res(Ac)-2-succinate-Vit E)

The solution of 3,5-resveratrol diacetate (1.2) (2.21 g), triethylamine (1.1 eq) and DMAP (0.2 eq) in THF (10 ml) is poured directly into the solution of tocopherylsuccinate chloride in CH$_2$Cl$_2$ obtained previously in step b).

A quantitative yield of the crude product is obtained. After purification on a silica column with a mixture of ethyl acetate/cyclohexane 30/70 v/v as eluent, a yield of 55% of resveratrol diacetate-succinate-Vit E is obtained with a molar purity of 98% analysed by NMR.

NMR $^1$H(CDCl$_3$/HMDS; 300 MHz): 0.80 (m, 12H); 1.04-1.49 (m, 24H); 1.72 (m, 2H); 1.92 (s, 3H); 1.96 (s, 3H); 2.03 (s, 3H); 2.24 (s, 6H); 2.53 (t, 6.6 Hz, 2H); 2.97 (m, 4H); 6.77 (t, 2.2 Hz, 1H); 6.89 (d, 16.2 Hz, 1H); 6.99 (d, 16.2 Hz, 1H); 7.03 (d, 8.5 Hz, 2H); 7.05 (d, 2.2 Hz, 2H); 7.41 (d, 8.5 Hz, 2H).

NMR $^{13}$C(CDCl$_3$/TMS; 75 MHz): 11.7 (CH$_3$Ph); 12.0 (CH$_3$Ph); 12.9 (CH$_3$Ph); 19.6 (2CH$_3$ chain); 20.5 (CH$_3$ ring); 21.0 (CH$_2$ chain); 21.0 (2CH$_3$C=O); 22.6 (CH$_3$ chain); 22.6 (CH$_3$ chain); 23.9 (CH$_3$ ring); 24.4 (CH$_2$ chain); 24.7 (CH$_2$ chain); ((2.8 CH$_2$ cyclohexane)); 27.9 (CH chain); 28.7 (CH$_2$C=O); 29.2 (CH$_2$C=O); 31.0 (CH$_2$ ring); 32.6 (CH chain); 32.7 (CH chain); 37.5 (4-CH$_2$ chain); 39.3 (CH$_2$ chain); 39.9 (CH$_2$ chain); 75.0 (Q ring); 114.3 (CH arom); 116.8 (2CH arom); 117.3 (Q arom); 121.8 (2CH arom); 123.0 (Q arom); 124.9 (Q arom); 126.6 (Q arom); 127.1 (CH ethylenic); 127.6 (CH arom); 129.6 (CH ethylenic); 134.5 (Q arom); 1395 (Q arom); 140.4 (Q arom); 149.4 (Q arom); 150.3 (Q arom); 151.2 (Q arom); 168.9 (2COCH$_3$); 170.7 (COOPh); 170.7 (COOPh).

EXAMPLE 4

Synthesis of 7-acetoxy-2-(3,4-diacetoxyphenyl)-4-oxo-4H-chromen-5-yl 2,5,7,8-tetramethyl-2-(4,8,12-trimethyltridecyl)-3,4-dihydro-2H-chromen-6-yl succinate (luteolin triacetate-succinyltocopheryl=Lut(Ac)$_3$-succinate-Vit E)

The mixed ester of luteolin and vitamin E (luteolin triacetate-monosuccinyltocopheryl) is obtained in four steps by esterification of luteolin triacetate with vitamin E succinate chloride in the presence of triethylamine and DMAP in THF at 0° C.

a) Synthesis of 3',4',7-luteolin triacetate(Lut(Ac)$_3$)

Onto a suspension of luteolin (40.8 g, 0.14 mole) in tert-butylmethylether (1 l, 60 eq), triethylamine (3.5 eq, 68 ml) is poured quickly, then acetic anhydride (3.1 eq, 41 ml) is poured on slowly under argon and at ambient temperature. The medium is then heated to 50° C. for 2 hours. After filtration of the reaction medium, the product obtained is taken up in dichloromethane, then washed twice with a 5% v/v HCl solution. The organic phase is dried over magnesium sulphate. After evaporation of the solvent, luteolin triacetate is obtained with a yield of 80% and a molar purity measured by NMR of the proton of 85.5%.

NMR $^1$H(CDCl$_3$, HMDS, 300 MHz): 2.25 (s, 6H); 2.27 (s, 3H); 6.51 (d, 2.2 Hz, 1H); 6.60 (s, 1H); 6.78 (d, 2.2 Hz, 11H); 7.30 (d, 8.2 Hz, 1H); 7.66 (m, 1H); 7.68 (dd, 8.2 and 2.2 Hz, 1H); 12.53 (s).

$^{13}$C(CDCl$_3$, TMS, 75 MHz): 20.5 (CH$_3$CO); 20.6 (CH$_3$CO); 21.1 (CH$_3$CO); 100.9 (CH arom); 105.5 (CH arom), 106.4 (CHCO); 108.7 (Q arom); 121.8 (CH arom); 124.3 (CH arom); 124.6 (CH arom); 129.4 (Q arom); 142.6 (Q arom); 145.1 (Q arom); 156.0 (Q arom); 156.5 (Q arom); 161.8 (Q arom); 162.7 (Q arom); 167.6 (COAc); 167.8 (COAc); 168.2 (COAc).

b) Synthesis of luteolin triacetate-succinyltocopheryl (Lut(Ac)-3-succinate-Vit E)

Triethylamine (0.75 ml, 1.1 eq) and 4-DMAP (120 mg, 0.2 eq) are added to a suspension of luteolin triacetate (2.28 g, 5.5 mmol) in 50 ml dichloromethane. Then 1 equivalent of the solution of α-tocopherylsuccinate chloride obtained as described previously is poured in slowly under argon and at ambient temperature. After 17 hours of reaction, the suspension obtained is taken up in dichloromethane, then washed twice with a 5% v/v HCl solution. The organic phase is then dried over magnesium sulphate. After evaporation of the solvent, 3.4 g are obtained, that is to say a yield of 52%.

$^1$H(CDCl$_3$, HMDS, 300 MHz): 0.80 (m, 12H); 1.04-1.5 (m, 24H); 1.72 (m, 2H); 1.90 (s, 3H); 1.95 (s, 3H); 2.01 (s, 3H); 2.28 (s, 9H); 2.52 (t, 6.8 Hz, 2H); 2.96 (m, 4H); 6.54 (s, 1H); 6.78 (m-car mixture, 11H); 7.28 (m-car mixture, 2H); 7.66 (m, 2H).

COMPARATIVE EXAMPLE 5

Synthesis of 3,5,4'-resveratrol tricaproate(Res(caproate)$_3$)

Resveratrol tricaproate (trihexanoate) is obtained by esterification of resveratrol with hexanoyl chloride in the presence of triethylamine in THF at ambient temperature. Triethylamine (8 ml; 3.3 eq) is added dropwise to a solution of resveratrol (4 g; 17.5 mmol) in THF (100 ml) whilst stirring at ambient temperature. The reaction medium is cooled to 0° C. and hexanoyl chloride (8.2 ml; 3 eq) is added dropwise. The reaction medium is stirred at temperature for 72 h. The medium is then washed with three times 30 ml of saturated solution of bicarbonate (pH 11). The phase aqueous is extracted with dichloromethane and this organic phase is dried over anhydrous MgSO$_4$. After concentration under reduced pressure, 5.2 g of a yellow oil are recovered with a purity per unit of mass dosed measured by NMR of 82%. The pure product is obtained with a yield of 80% after purification on a silica column with ethyl acetate/cyclohexane (20/80 v/v) as eluent.

$^1$H (DMSO, HMDS, 300 MHz): 0.85 (m, 9H); 1.28 (m, 12H); 1.59 (m, 6H); 2.52 (m, 6H); 6.82 (t, 2.2 Hz, 1H); 7.07 (d, 8.8 Hz, 2H); 7.16 (d, 16.7 Hz, 1H); 7.21 (d, 2.2 Hz, 2H); 7.28 (d, 16.7 Hz, 1H); 7.57 (d, 8.8 Hz, 2H).

EXAMPLE 6

Synthesis of 3,5-resveratrol diacetate-4'-caproate (6)

Compound 6 is synthesised as described in Example 1, by replacing the lipoic acid chloride by hexanoyl(caproyl) chloride. Resveratrol diacetate (4 g, 12.8 mmol) which has been solubilised in 60 ml of anhydrous THF is added. Triethylamine (1.5 eq) is added dropwise, then hexanoyl chloride (2.72 ml; 1.5 eq) in an ice bath (0° C.). After 17 h of stirring at ambient temperature, the medium is transferred into a separation funnel, washed with 10 ml of a saturated solution of bicarbonate, then extracted with three times 20 ml of ethyl acetate. The organic phase is washed with three times 20 ml of water, then dried over anhydrous $MgSO_4$. The crude product is obtained after concentration under reduced pressure with a yield of 90% and a purity per unit of mass of 80%.

$^1H(CDCl_3$, HMDS, 300 MHz): 0.87 (m, 3H), 1.2-1.3 (m, 4H); 1.69 (m, 2H); 2.23 (s, 6H); 2.48 (t, 7.7 Hz, 2H); 6.75 (t, 1.9 Hz, 1H); 6.89 (d, 15.9 Hz, 1H); 6.99 (d, 15.9 Hz, 1H); 7.01 (d, 8.5 Hz, 2H); 7.04 (d, 1.9 Hz, 2H); 7.41 (d, 8.5 Hz, 2H).

COMPARATIVE EXAMPLE 7

Synthesis of 3,5,4'-resveratrol trilipoate(Res(Lipoate)$_3$)

Resveratrol trilipoate is obtained via lipoic acid chloride prepared in situ under argon at ambient temperature in dichloromethane. The acylation reaction leads to a mixture of the products of coupling (phenolic and recorcinic monolipoates, dilipoates and trilipoates). The trilipoates were obtained after chromatography on silica. The product was not characterised for reasons of insolubility. For the same reasons it cannot be bio-hydrolysed (see Table 1).

EXAMPLE 8

Preparation of Enzymatic Extract

The enzymes used in the bio-hydrolysis trials in vitro were obtained by the method of "tape stripping" as described in the literature (*Anal. Biochem.*, 290, (2001), 179-185; *Skin Pharmacol. Appl. Skin Physiol.*, 12, (1999), 182-192). Samples of *Stratum corneum* are taken with surgical sparadrap (type Blenderm 3M Health Care, St. Paul, Minn., USA). The buffers used in the bio-hydrolysis trials are: 50 mM Tris(tris[hydroxymethyl]aminomethane) pH 7.3 and pH 8; 50 mM Na-acetate pH 5.5; 50 mM MES (2-[N-morpholino]-ethanesulphonic) acid pH 6 and 50 mM phosphate pH 6.5.

EXAMPLE 9

Bio-Hydrolysis a. Bio-Hydrolysis with the Cutaneous Enzymes Obtained by Tape Stripping The precursors are solubilised in acetonitrile at a concentration of 1 g/l. For the bio-hydrolysis trials 50 µl of substrate and 50 µl of acetonitrile in 900 µl of enzymatic extract in the buffer at a chosen pH are added. The reaction mixtures are incubated at 35° C. without stirring and shielded from the light. The evolution of the bio-hydrolysis is determined by HPLC (high-performance liquid chromatography) with reverse phase polarity. The controls are effected in the same solutions without enzymatic extracts of skin, in order to determine the chemical stability of the products.

b) Bio-Hydrolysis with Animal Cholesterol Esterase

The enzyme used is the cholesterol esterase of bovine pancreas, of E.C. class 3.1.1.13 (SIGMA C-3766). The precursors are prepared as described in Example 9a. The results are presented in Table 1 below.

TABLE 1

| Substrate (Precursor) | Enzyme | Bio-hydrolysis time (h) | Bio-hydrolysis Rate (%) | Active substance(s) released by bio-hydrolyse | | |
|---|---|---|---|---|---|---|
| | | | | Polyphenol (PP) | A | B |
| Res(caproate)$_3$ | Stratum corneum | 168 | 98 | Resveratrol | Caproate | |
| Res(Ac)$_2$-caproate | Stratum corneum | 72 | 95 | Resveratrol | Acetate + Caproate | |
| Res(lipoate)$_3$ * | * | | | | | |
| Res(Ac)$_2$-lipoate | Stratum corneum | 48 | 87 | Resveratrol + lipoic acid | Acetate | Lipoate |
| Res(Ac)$_2$-succinate-Vit E ** | Stratum corneum | 96 | 26 | Res-succinate-Vit E ** | Acetate | |
| Res(Ac)$_2$-succinate-Vit E | animal Cholesterol esterase | 2 24 | 80 99 | Resveratrol | Acetate + Succinate | Vitamin E |
| Res(Ac)$_2$-ferulate(Ac) | Stratum corneum | 6.5 | 71 | Resveratrol | Acetate | Ferulic acid |
| Lut(Ac)$_3$-succinate-Vit E | Stratum corneum | 5 | 70 | Luteolin | Acetate + Succinate | Vitamin E |

* Reaction not carried out because precursor insoluble in the medium
** the lipases of the Stratum corneum hydrolyse the acetyl groups of the precursor and lead to an intermediate (Res-succinate-Vit E) which itself has an antioxidant activity by virtue of the OH group of the di-acetyl resveratrol part Esterases are naturally present in the *Stratum granulosum*. The examples with Res(Ac)-2-succinate-Vit E show the potential for release of the active substances in the skin, with the action of the enzymes of the *Stratum corneum* on the acetate groups, enabling rapid release of the antioxidant power of the alcohol groups, then the action of the enzymes of the *Stratum granulosum* on the separation of the active substances.

EXAMPLE 10

Oil in Water Formulation

A 1% formulation of Res(Ac)-2-Lipoate (compound of Example 1 according to the invention) of the oil-in-water type having the following composition (the percentages are expressed by weight):

| | |
|---|---|
| Water | 78.90 |
| Tetrasodium EDTA | 0.10 |
| 1,3-butylene glycol | 5.00 |
| Emulium Delta ® [1] | 4.00 |
| Ethylhexyl palmitate | 5.00 |
| Cetyl alcohol | 0.20 |
| Dimethicone | 3.00 |
| Phenonip ® [2] | 1.00 |
| 2-DL-tocopherol acetate | 0.30 |
| Res(Ac)$_2$-Lipoate according to the invention | 1.00 |
| 50% citric acid | 0.08 |
| Water | 0.92 |

[1] Emulium Delta ®: Cetyl alcohol + glyceryl stearate + stearate of PEG-75 + ceteth-20 + steareth-20.
[2] Phenonip ®: phenoxyethanol + methylparaben + ethylparaben + butylparaben + propylparaben + isobutylparaben.

The formulation thus obtained exhibits good stability after 56 days in the oven at 45° C.

EXAMPLE 11

Examples of Formulations

The following formulations are provided purely by way of illustration. The percentages are expressed by weight, relative to the total weight of the composition.

Formulation 11.1: Anhydrous Formulation

| INCI Name | Quantity |
|---|---|
| SODIUM SURFACTIN | 0.50 |
| GLYCERIN | 24.90 |
| 1,3 BUTYLENE GLYCOL | 7.50 |
| CYCLOMETHICONE 5 | 14.00 |
| DIMETHICONE 5 | 10.00 |
| ISONONYL ISONANOATE | 10.00 |
| *LIMNANTHES ALBA* | 10.00 |
| ISODODECANE | 13.00 |
| CETIOL CC | 10.00 |
| Bioprecursor according to example 1 | 0.10 |
| Total | 100.00 |

Formulation 11.2: Water in Oil (W/O) Formulation

| INCI Name | Quantity |
|---|---|
| ETHYLHEXYL PALMITATE | 14.00 |
| PROPYLPARABEN | 0.30 |
| PEG-30 DIPOLYHYDROXYSTEARATE | 3.00 |
| SILICA DIMETHYL SILYLATE | 2.00 |
| HYDROGENATED POLYISOBUTENE | 31.49 |
| ETHYLENE/PROPYLENE/STYRENE COPOLYMER | 2.62 |
| BUTYLENE/ETHYLENE/STYRENE COPOLYMER | 0.88 |
| BHT | 0.01 |
| AQUA | 42.10 |
| SODIUM CHLORIDE | 0.80 |
| TETRASODIUM EDTA | 0.05 |
| GLYCERIN | 2.00 |
| METHYLPARABEN | 0.30 |
| XANTHAN GUM | 0.35 |
| Bioprecursor according to example 1 | 0.10 |
| Total | 100.00 |

Formulation 11.3: W/Si Formulation

| INCI Name | Quantity |
|---|---|
| CYCLOPENTASILOXANE | 24.25 |
| PEG/PPG-20/15 DIMETHICONE | 1.00 |
| DIMETHICONE | 5.00 |
| C$_{30-45}$ ALKYL CETEARYL DIMETHICONE CROSSPOLYMER | 2.25 |
| TOCOPHERYL ACETATE | 0.30 |
| PHENOXYETHANOL | 0.72 |
| METHYLPARABEN | 0.16 |
| ETHYLPARABEN | 0.04 |
| BUTYLPARABEN | 0.04 |
| PROPYLPARABEN | 0.02 |
| ISOBUTYLPARABEN | 0.02 |
| AQUA (WATER) | 58.10 |
| SODIUM CHLORIDE | 1.00 |
| POLYSORBATE-20 | 1.00 |
| BUTYLENE GLYCOL | 3.00 |
| GLYCERIN | 3.00 |
| Bioprecursor according to example 1 | 0.10 |
| Total | 100.00 |

Formulation 11.4: Formulation of Serum Type

| INCI Name | Quantity |
|---|---|
| AQUA (WATER) | 85.19 |
| TETRASODIUM EDTA | 0.05 |
| POLYETHYLENEGLYCOL | 5.00 |
| ACRYLATES/C10-30 ALKYL ACRYLATE CROSSPOLYMER | 0.35 |
| AMMONIUM ACRYLOYLDIMETHYLTAURATE/VP COPOLYMER | 0.30 |
| GLYCERIN | 4.43 |
| PEG-8 | 1.00 |
| SODIUM POLYACRYLATE | 0.04 |
| CAPRYLYL GLYCOL | 0.15 |
| PEG-11 METHYL ETHER DIMETHICONE | 3.00 |
| PROPYLENE GLYCOL | 0.01 |
| PROPYLPARABEN | 0.01 |
| METHYLPARABEN | 0.31 |
| SODIUM HYDROXIDE | 0.06 |
| Bioprecursor according to example 1 | 0.10 |
| Total | 100.00 |

Formulation 11.5: Formulation of Serum Type WSi

| INCI Name | Quantity |
|---|---|
| CYCLOPENTASILOXANE | 28.97 |
| PEG/PPG-18/18 DIMETHICONE | 0.90 |
| CYCLOHEXASILOXANE | 4.38 |
| SORBITAN SESQUIOLEATE | 0.50 |
| PEG-45/DODECYL GLYCOL COPOLYMER | 1.00 |
| ISOCETYL STEARATE | 1.00 |
| HYDROGENATED CASTOR OIL | 0.25 |
| C30-45 ALKYL CETEARYL DIMETHICONE CROSSPOLYMER | 2.25 |
| BHT | 0.01 |
| ASCORBYL PALMITATE | 0.01 |
| GLYCERYL STEARATE | 0.01 |
| GLYCERIN | 1.50 |
| PROPYLENE GLYCOL | 1.50 |
| AQUA (WATER) | 48.06 |
| TETRASODIUM EDTA | 0.05 |
| SCLEROTIUM GUM | 0.20 |
| SODIUM CHLORIDE | 0.80 |
| HDI/TRIMETHYLOL HEXYLLACTONE CROSSPOLYMER | 2.45 |
| SILICA | 2.55 |
| ALCOHOL DENAT | 3.00 |
| METHYLPARABEN | 0.25 |
| CHLORPHENESIN | 0.26 |
| Bioprecursor according to example 1 | 0.10 |
| Total | 100.00 |

Formulation 11.6: Hydro-Alcoholic Gel Formulation

| INCI Name | Quantity |
| --- | --- |
| AQUA (WATER) | 56.95 |
| TETRASODIUM EDTA | 0.05 |
| ACRYLATES/VINYL ISODECANOATE CROSPOLYMER | 0.50 |
| GLYCERIN | 5.00 |
| PROPYLENE GLYCOL | 8.00 |
| ACRYLATES/$C_{10-30}$ ALKYL ACRYLATE CROSSPOLYMER | 0.20 |
| PENTYLENE GLYCOL | 6.00 |
| CYCLOPENTASILOXANE | 6.00 |
| DIMETHICONE | 1.74 |
| DIMETHICONOL | 0.26 |
| ALCOHOL DENAT | 15.00 |
| TETRAHYDROXYPROPYL ETHYLENEDIAMINE | 0.20 |
| Bioprecursor according to example 1 | 0.10 |
| Total | 100.00 |

Formulation 11.7: Gel-Cream Formulation

| INCI Name | Quantity |
| --- | --- |
| AQUA (WATER) | 75.36 |
| TETRASODIUM EDTA | 0.05 |
| GLYCERIN | 7.26 |
| AMMONIUM ACRYLOYLDIMETHYLTAURATE/VP COPOLYMER | 0.80 |
| ACRYLATES/C10-30 ALKYL ACRYLATE CROSSPOLYMER | 0.15 |
| METHYLPARABEN | 0.30 |
| CYCLOTETRASILOXANE | 0.02 |
| POLYSORBATE-20 | 0.05 |
| ISONONYL ISONANOATE | 3.00 |
| CYCLOPENTASILOXANE | 5.23 |
| CYCLOHEXASILOXANE | 2.80 |
| DIMETHICONE | 2.00 |
| PHENYL TRIMETHICONE | 2.00 |
| TOCOPHERYL ACETATE | 0.50 |
| POLYACRYLAMIDE | 0.12 |
| HYDROGENATED POLYISOBUTENE | 0.05 |
| LAURETH-7 | 0.02 |
| HYDROXYETHYL ACRYLATE/SODIUM ACRYLOYLDIMETHYL TAURATE COPOLYMER | 0.09 |
| SQUALANE | 0.06 |
| POLYSORBATE 60 | 0.01 |
| SORBITAN ISOSTEARATE | 0.01 |
| SODIUM HYDROXIDE | 0.02 |
| Bioprecursor according to example 1 | 0.10 |
| Total | 100.00 |

Formulation 11.8: Anhydrous Formulation

| INCI Name | Quantity |
| --- | --- |
| SODIUM SURFACTIN | 0.50 |
| GLYCERIN | 24.90 |
| 1,3 BUTYLENE GLYCOL | 750 |
| CYCLOMETHICONE 5 | 14.00 |
| DIMETHICONE 5 | 10.00 |
| ISONANOATE ISONONYLE | 10.00 |
| *LIMNANTHES ALBA* | 10.00 |
| ISODODECANE | 13.00 |
| CETIOL CC | 10.00 |
| Bioprecursor according to example 3 | 0.10 |
| Total | 100.00 |

Formulation 11.9: Water in Oil (W/O) Formulation

| INCI Name | Quantity |
| --- | --- |
| ETHYLHEXYL PALMITATE | 1.00 |
| PROPYLPARABEN | 0.30 |
| PEG-30 DIPOLYHYDROXYSTEARATE | 3.00 |
| SILICA DIMETHYL SILYLATE | 2.00 |
| HYDROGENATED POLYISOBUTENE | 31.49 |
| ETHYLENE/PROPYLENE/STYRENE COPOLYMER | 2.62 |
| BUTYLENE/ETHYLENE/STYRENE COPOLYMER | 0.88 |
| BHT | 0.01 |
| AQUA | 42.10 |
| SODIUM CHLORIDE | 0.80 |
| TETRASODIUM EDTA | 0.05 |
| GLYCERIN | 2.00 |
| METHYLPARABEN | 0.30 |
| XANTHAN GUM | 0.35 |
| Bioprecursor according to example 3 | 0.10 |
| Total | 100.00 |

Formulation 11.10: W/Si Formulation

| INCI Name | Quantity |
| --- | --- |
| CYCLOPENTASILOXANE | 24.25 |
| PEG/PPG-20/15 DIMETHICONE | 1.00 |
| DIMETHICONE | 5.00 |
| $C_{30-45}$ ALKYL CETEARYL DIMETHICONE CROSSPOLYMER | 2.25 |
| TOCOPHERYL ACETATE | 0.30 |
| PHENOXYETHANOL | 0.72 |
| METHYLPARABEN | 0.16 |
| ETHYLPARABEN | 0.04 |
| BUTYLPARABEN | 0.04 |
| PROPYLPARABEN | 0.02 |
| ISOBUTYLPARABEN | 0.02 |
| AQUA (WATER) | 58.10 |
| SODIUM CHLORIDE | 1.00 |
| POLYSORBATE-20 | 1.00 |
| BUTYLENE GLYCOL | 3.00 |
| GLYCERIN | 3.00 |
| Bioprecursor according to example 3 | 0.10 |
| Total | 100.00 |

Formulation 11.11: Formulation of serum type

| INCI Name | Quantity |
| --- | --- |
| AQUA (WATER) | 85.19 |
| TETRASODIUM EDTA | 0.05 |
| POLYETHYLENEGLYCOL | 5.00 |
| ACRYLATES/C10-30 ALKYL ACRYLATE CROSSPOLYMER | 0.35 |
| AMMONIUM ACRYLOYLDIMETHYLTAURATE/VP COPOLYMER | 0.30 |
| GLYCERIN | 4.43 |
| PEG-8 | 1.00 |
| SODIUM POLYACRYLATE | 0.04 |
| CAPRYLYL GLYCOL | 0.15 |
| PEG-11 METHYL ETHER DIMETHICONE | 3.00 |
| PROPYLENE GLYCOL | 0.01 |
| PROPYLPARABEN | 0.01 |
| METHYLPARABEN | 0.31 |
| SODIUM HYDROXIDE | 0.06 |
| Bioprecursor according to example 3 | 0.10 |
| Total | 100.00 |

23

Formulation 11.12: Formulation of Serum Type W/Si

| INCI Name | Quantity |
|---|---|
| CYCLOPENTASILOXANE | 28.97 |
| PEG/PPG-18/18 DIMETHICONE | 0.90 |
| CYCLOHEXASILOXANE | 4.38 |
| SORBITAN SESQUIOLEATE | 0.50 |
| PEG-45/DODECYL GLYCOL COPOLYMER | 1.00 |
| ISOCETYL STEARATE | 1.00 |
| HYDROGENATED CASTOR OIL | 0.25 |
| C30-45 ALKYL CETEARYL DIMETHICONE CROSSPOLYMER | 2.25 |
| BHT | 0.01 |
| ASCORBYL PALMITATE | 0.01 |
| GLYCERYL STEARATE | 0.01 |
| GLYCERIN | 1.50 |
| PROPYLENE GLYCOL | 1.50 |
| AQUA (WATER) | 48.06 |
| TETRASODIUM EDTA | 0.05 |
| SCLEROTIUM GUM | 0.20 |
| SODIUM CHLORIDE | 0.80 |
| HDI/TRIMETHYLOL HEXYLLACTONE CROSSPOLYMER | 2.45 |
| SILICA | 2.55 |
| ALCOHOL DENAT | 3.00 |
| METHYLPARABEN | 0.25 |
| CHLORPHENESIN | 0.26 |
| Bioprecursor according to example 3 | 0.10 |
| Total | 100.00 |

Formulation 11.13: Hydro-Alcoholic Gel Formulation

| INCI Name | Quantity |
|---|---|
| AQUA (WATER) | 56.95 |
| TETRASODIUM EDTA | 0.05 |
| ACRYLATES/VINYL ISODECANOATE CROSSPOLYMER | 0.50 |
| GLYCERIN | 5.00 |
| PROPYLENE GLYCOL | 8.00 |
| ACRYLATES/C$_{10-30}$ ALKYL ACRYLATE CROSSPOLYMER | 0.20 |
| PENTYLENE GLYCOL | 6.00 |
| CYCLOPENTASILOXANE | 6.00 |
| DIMETHICONE | 1.74 |
| DIMETHICONOL | 0.26 |
| ALCOHOL DENAT | 15.00 |
| TETRAHYDROXYPROPYL ETHYLENEDIAMINE | 0.20 |
| Bioprecursor according to example 3 | 0.10 |
| Total | 100.00 |

Formulation 11.14: Gel-Cream Formulation

| INCI Name | Quantity |
|---|---|
| AQUA (WATER) | 75.36 |
| TETRASODIUM EDTA | 0.05 |
| GLYCERIN | 7.26 |
| AMMONIUM ACRYLOYLDIMETHYLTAURATE/VP COPOLYMER | 0.80 |
| ACRYLATES/C10-30 ALKYL ACRYLATE CROSSPOLYMER | 0.15 |
| METHYLPARABEN | 0.30 |
| CYCLOTETRASILOXANE | 0.02 |
| POLYSORBATE-20 | 0.05 |
| ISONONYL ISONANOATE | 3.00 |
| CYCLOPENTASILOXANE | 5.23 |
| CYCLOHEXASILOXANE | 2.80 |
| DIMETHICONE | 2.00 |
| PHENYL TRIMETHICONE | 2.00 |
| TOCOPHERYL ACETATE | 0.50 |
| POLYACRYLAMIDE | 0.12 |

24

-continued

| INCI Name | Quantity |
|---|---|
| HYDROGENATED POLYISOBUTENE | 0.05 |
| LAURETH-7 | 0.02 |
| HYDROXYETHYL ACRYLATE/SODIUM ACRYLOYLDIMETHYL TAURATE COPOLYMER | 0.09 |
| SQUALANE | 0.06 |
| POLYSORBATE 60 | 0.01 |
| SORBITAN ISOSTEARATE | 0.01 |
| SODIUM HYDROXIDE | 0.02 |
| Bioprecursor according to example 3 | 0.10 |
| Total | 100.00 |

It should be readily understood that the invention defined by the appended claims is not limited to the particular embodiments indicated in the above description, but encompasses the variants thereof which do not go beyond the scope nor the spirit of the present invention.

The invention claimed is:

1. A topically applicable formulation useful for the preparation of a therapeutic, dermatological or cosmetic composition, comprising a bioprecursor having the structural formula:

[A]$_n$-PP-[B]$_m$ in which:

PP is a polyphenol radical having the following formula:

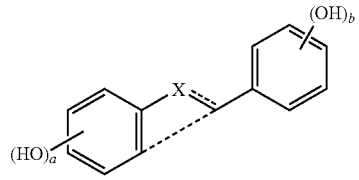

in which:
a is 1, 2, 3, 4 or 5;
b is 1, 2, 3, 4 or 5;
X is N, S, O, CH, CH$_2$, CO or NH;
----- is a double or a single bond;
----- is a linking chain which may be present, forming a 5- or 6-membered ring, including X and having one or more double bonds, optionally one or more OH substituents and/or one or more heteroatoms selected from among N, S, O, which are situated in the ring and/or substitute therefor;

or having the following formula:

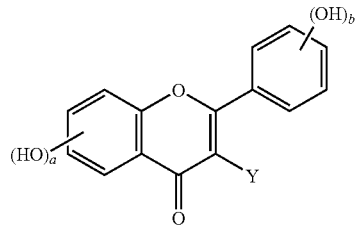

in which:
Y is H or OH, a is 1, 2, 3, or 4 and b is 1, 2, 3, 4 or 5, in which each hydroxyl function is protected by a group A or a group B;

A is a substituted or unsubstituted, saturated or unsaturated alkyl radical having from 1 to 20 carbon atoms, which is bonded to the polyphenol by:
a carboxylic ester function on a hydroxyl function of the said polyphenol; or
by means of an A' spacer, in which A is bonded to A' via a carboxylic ester function, and A' is bonded to the polyphenol via a carboxylic ester function on a hydroxyl function of the said polyphenol;
n is an integer greater than or equal to 1;
B is a precursor of a biologically active molecule which is bonded to the polyphenol by:
a carboxylic ester function on a hydroxyl function of the said polyphenol; or
by means of a B' spacer, in which B is bonded to B' via a carboxylic ester function, and B' is bonded to the polyphenol by a carboxylic ester function on a hydroxyl function of the said polyphenol; and
m is an integer greater than or equal to 1,
wherein the biologically active molecule is selected from the group consisting of lipoic acid, vitamins A, B, D, E, retinoic acids, and hydroxyacids; and wherein the groups A' and B' of the bioprecursor are, independently of one another, an aliphatic hydrocarbon chain comprising two acid functions or one acid function and one hydroxyl function having from 2 to 13 carbon atoms.

2. The topically applicable formulation as defined by claim 1, wherein said polyphenol has the following formula:

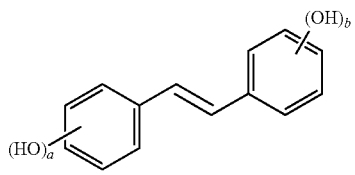

in which:
a is 1, 2, 3, 4 or 5 and b is 1, 2, 3, 4 or 5.

3. The topically applicable formulation as defined by claim 2, wherein a is 2 and b is 1.

4. The topically applicable formulation as defined by claim 1, wherein the polyphenol has the following formula:

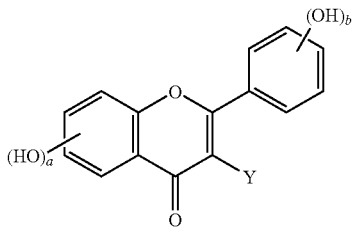

in which:
Y is H or OH, a is 2 and b is 2.

5. The topically applicable formulation as defined by claim 1, wherein said polyphenol is selected from the group consisting of resveratrol, luteolin, quercetin, hydroquinone, pyrocatechol, gallic acid, hydroxytyrosol, tetrahydrocurcumin, silymarin and ellagic acid.

6. The topically applicable formulation as defined by claim 1, wherein the group A of the bioprecursor is derived from a linear, branched or cyclic carboxylic acid, selected from the group consisting of ethanoic acid, propanoic acid, linear or branched butanoic acid, caproic acid and lauric acid.

7. The topically applicable formulation as defined by claim 1, wherein A' and B' are independently of one another a succinic acid, adipic acid, brassylic acid, lactic acid, salicylic acid, 4-hydroxybenzoic acid, ferulic acid, tartaric acid, 2-hydroxybutanoic acid, 3-hydroxybutanoic acid or 4-hydroxybutanoic acid radical.

8. The topically applicable formulation as defined by claim 1, wherein said bioprecursor is selected from the group consisting of:
(E)-4-(3,5-diacetoxystyryl)phenyl-5-(1,2-dithiolan-3-yl) pentanoate;
(E)-4-(3,5-diacetoxystyryl)phenyl-2,5,7,8-tetramethyl-2-(4,8,12-trimethyltridecyl)-3,4-dihydro-2H-chromen-6-yl succinate;
4-((E)-3,5-diacetoxystyryl)phenyl-(2Z,4E,6Z,8E)-3,7-dimethyl-9-(2,6,6-trimethylcyclohex-1-enyl)nona-2,4,6,8-tetraenyl succinate;
(2E,4E,6E,8E,10E,12E)-4-((E)-3,5-diacetoxystyryl)phenyl docosa-2,4,6,8,10,12-hexaenoate;
(E)-4-(3,5-diacetoxystyryl)phenyl 4-hydroxy-3-methoxybenzoate;
(E)-4-(3,5-diacetoxystyryl)phenyl 3,4-diacetoxybenzoate;
(E)-4-((E)-3,5-diacetoxystyryl)phenyl 3-(4-hydroxy-3-methoxyphenyl)acrylate;
(E)-4-((E)-3,5-diacetoxystyryl)phenyl 3-(4-acetoxy-3-methoxyphenyl)acrylate;
(E)-4-((E)-3,5-diacetoxystyryl)phenyl 3-(4-methoxyphenyl)acrylate;
(E)-4-(3,5-diacetoxystyryl)phenyl 2-acetoxybenzoate;
7-acetoxy-2-(3,4-diacetoxyphenyl)-4-oxo-4H-chromen-5-yl 5-(1,2-dithiolan-3-yl)pentanoate;
7-acetoxy-2-(3,4-diacetoxyphenyl)-4-oxo-4H-chromen-5-yl 2,5,7,8-tetramethyl-2-(4,8,12-trimethyltridecyl)-3,4-dihydro-2H-chromen-6-yl succinate;
2-methoxy-4-(7-(3-methoxy-4-(prop-1-en-2-yloxy)phenyl)-3,5-dioxoheptyl)-phenyl 5-(1,2-dithiolan-3-yl) pentanoate; and
2-methoxy-4-(7-(3-methoxy-4-(prop-1-en-2-yloxy)phenyl)-3,5-dioxoheptyl)-phenyl 2,5,7,8-tetramethyl-2-(4,8,12-trimethyltridecyl)-3,4-dihydro-2H-chromen-6-yl succinate.

9. The topically applicable formulation as defined by claim 8, wherein said bioprecursor is selected from among (E)-4-(3,5-diacetoxystyryl)phenyl-5-(1,2-dithiolan-3-yl)pentanoate and (E)-4-(3,5-diacetoxystyryl)phenyl-2,5,7,8-tetramethyl-2-(4,8,12-trimethyltridecyl)-3,4-dihydro-2H-chromen-6-yl succinate.

10. A bioprecursor having the structural formula:

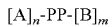
$[A]_n$-PP-$[B]_m$ in which:
PP is a polyphenol radical
having the following formula:

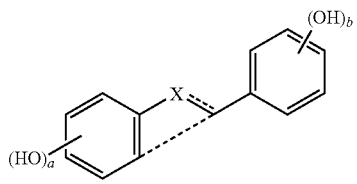

in which:
  a is 1, 2, 3, 4 or 5;
  b is 1, 2, 3, 4 or 5;
  X is N, S, O, CH, CH$_2$, CO or NH;
  ----- is a double or a single bond;
  ----- is a linking chain which may be present, forming a 5- or 6-membered ring, including X and having one or more double bonds, optionally one or more OH substituents and/or one or more heteroatoms selected from among N, S, O, which are situated in the ring and/or substitute therefor;
or
having the following formula:

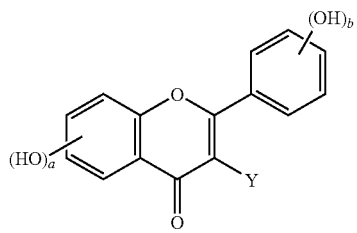

in which:
  Y is H or OH, a is 1, 2, 3, or 4 and b is 1, 2, 3, 4 or 5, in which each hydroxyl function is protected by a group A or a group B;
  A is a substituted or unsubstituted, saturated or unsaturated alkyl radical having from 1 to 20 carbon atoms, which is bonded to the polyphenol by:
  a carboxylic ester function on a hydroxyl function of the said polyphenol; or
  by means of an A' spacer, in which A is bonded to A' via a carboxylic ester function, and A' is bonded to the polyphenol via a carboxylic ester function on a hydroxyl function of the said polyphenol;
  n is an integer greater than or equal to 1;
  B is a precursor of a biologically active molecule which is bonded to the polyphenol by:
  a carboxylic ester function on a hydroxyl function of the said polyphenol; or
  by means of a B' spacer, in which B is bonded to B' via a carboxylic ester function, and B' is bonded to the polyphenol via a carboxylic ester function on a hydroxyl function of the said polyphenol; and
  m is an integer greater than or equal to 1,
wherein the biologically active molecule is selected from the group consisting of lipoic acid, vitamins A, B, D, E, retinoic acids, and hydroxyacids; and
wherein the groups A' and B' of the bioprecursor are, independently of one another, an aliphatic hydrocarbon chain comprising two acid functions or one acid function and one hydroxyl function having from 2 to 13 carbon atoms.

11. The bioprecursor as defined by claim 10, wherein said polyphenol has the following formula:

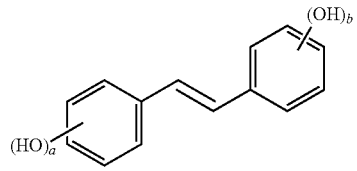

in which:
  a is 1, 2, 3, 4 or 5 and b is 1, 2, 3, 4 or 5.

12. The bioprecursor as defined by claim 11, wherein a is 2 and b is 1.

13. The bioprecursor as defined by claim 10, wherein the polyphenol has the following formula:

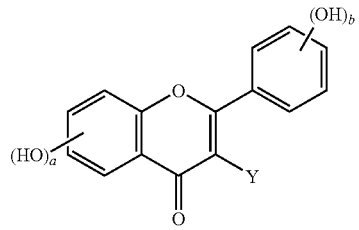

in which:
  Y is H or OH, a is 2 and b is 2.

14. The bioprecursor as defined by claim 10, wherein said polyphenol is selected from the group consisting of resveratrol, luteolin, quercetin, hydroquinone, pyrocatechol, gallic acid, hydroxytyrosol, tetrahydrocurcumin, silymarin and ellagic acid.

15. The bioprecursor as defined by claim 10, wherein the group A is derived from a linear, branched or cyclic carboxylic acid, selected from the group consisting of ethanoic acid, propanoic acid, linear or branched butanoic acid, caproic acid and lauric acid.

16. The bioprecursor as defined by claim 10, wherein A' and B' are independently of one another a succinic acid, adipic acid, brassylic acid, lactic acid, salicylic acid, 4-hydroxybenzoic acid, ferulic acid, tartaric acid, 2-hydroxybutanoic acid, 3-hydroxybutanoic acid or 4-hydroxybutanoic acid radical.

17. The bioprecursor as defined by claim 10, selected from the group consisting of:
  (E)-4-(3,5-diacetoxystyryl)phenyl-5-(1,2-dithiolan-3-yl) pentanoate;
  (E)-4-(3,5-diacetoxystyryl)phenyl-2,5,7,8-tetramethyl-2-(4,8,12-trimethyltridecyl)-3,4-dihydro-2H-chromen-6-yl succinate;
  4-((E)-3,5-diacetoxystyryl)phenyl-(2Z,4E,6Z,8E)-3,7-dimethyl-9-(2,6,6-trimethylcyclohex-1-enyl)nona-2,4,6,8-tetraenyl succinate;
  (2E,4E,6E,8E,10E,12E)-4-((E)-3,5-diacetoxystyryl)phenyl docosa-2,4,6,8,10,12-hexaenoate;
  (E)-4-(3,5-diacetoxystyryl)phenyl 4-hydroxy-3-methoxybenzoate;
  (E)-4-(3,5-diacetoxystyryl)phenyl 3,4-diacetoxybenzoate;
  (E)-4-((E)-3,5-diacetoxystyryl)phenyl 3-(4-hydroxy-3-methoxyphenyl)acrylate;
  (E)-4-((E)-3,5-diacetoxystyryl)phenyl 3-(4-acetoxy-3-methoxyphenyl)acrylate;
  (E)-4-((E)-3,5-diacetoxystyryl)phenyl 3-(4-methoxyphenyl)acrylate;
  (E)-4-(3,5-diacetoxystyryl)phenyl 2-acetoxybenzoate;
  7-acetoxy-2-(3,4-diacetoxyphenyl)-4-oxo-4H-chromen-5-yl5-(1,2-dithiolan-3-yl)pentanoate;
  7-acetoxy-2-(3,4-diacetoxyphenyl)-4-oxo-4H-chromen-5-yl2,5,7,8-tetramethyl-2-(4,8,12-trimethyltridecyl)-3,4-dihydro-2H-chromen-6-yl succinate;
  2-methoxy-4-(7-(3-methoxy-4-(prop-1-en-2-yloxy)phenyl)-3,5-dioxoheptyl)-phenyl 5-(1,2-dithiolan-3-yl) pentanoate; and 2-methoxy-4-(7-(3-methoxy-4-(prop-1-en-2-yloxy)phenyl)-3,5-dioxoheptyl)-phenyl 2,5,7,8-tetramethyl-2-(4,8,12-trimethyltridecyl)-3,4-dihydro-2H-chromen-6-yl succinate.

18. The bioprecursor as defined by claim 17, wherein said bioprecursor is (E)-4-(3,5-diacetoxystyryl)phenyl-5-(1,2-dithiolan-3-yl)pentanoate or (E)-4-(3,5-diacetoxystyryl)phenyl-2,5,7,8-tetramethyl-2-(4,8,12-trimethyltridecyl)-3,4-dihydro-2H-chromen-6-yl succinate.

19. A composition, comprising at least one bioprecursor as defined by claim 10, wherein B is a precursor of a dermatologically or cosmetically active molecule, formulated into a topically applicable, dermatologically/cosmetically acceptable medium therefor.

20. A composition, comprising at least one bioprecursor as defined by claim 10, wherein B is a precursor of a therapeutic molecule, formulated into a topically applicable, therapeutically acceptable medium therefor.

21. A method for applying a bioprecursor of a biologically active molecule having cosmetic or dermatological activity, comprising topically applying onto the skin of an individual in need of such treatment, a thus effective amount of the composition as defined by claim 19.

22. A method for applying a bioprecursor of a biologically active molecule having therapeutic activity, comprising topically applying onto the skin of an individual in need of such treatment, a thus effective amount of the composition as defined by claim 20.

23. A process for the preparation of a bioprecursor as defined by claim 10, comprising at least the following steps:
  a) protecting the polyphenol by preesterification with a compound A-Z, where Z comprises a function capable of reacting with an OH function of the polyphenol to generate the ester bond between the polyphenol and A,
  b) selectively deprotecting the polyphenol to obtain one or more free OH functions of the polyphenol, and
  c) coupling the intermediate obtained after the step b) with the biologically active B molecule previously activated.

* * * * *